US011707092B2

(12) United States Patent
Plattner et al.

(10) Patent No.: US 11,707,092 B2
(45) Date of Patent: Jul. 25, 2023

(54) AEROSOL GENERATING APPARATUSES WITH LOCATING MEMBER AND SUBSTANTIALLY SURROUNDING AIRFLOW PATH OF CONSUMABLE UNIT

(71) Applicant: JT International S.A., Geneva (CH)

(72) Inventors: Michael Plattner, Trier (DE); Thomas Johaentges, Schweich (DE); Takashi Hasegawa, Kanagawa (JP)

(73) Assignee: JT International S.A.

( * ) Notice: Subject to any disclaimer, the term of this patent is extended or adjusted under 35 U.S.C. 154(b) by 333 days.

(21) Appl. No.: 16/470,806

(22) PCT Filed: Dec. 29, 2017

(86) PCT No.: PCT/EP2017/084842
§ 371 (c)(1),
(2) Date: Jun. 18, 2019

(87) PCT Pub. No.: WO2018/122389
PCT Pub. Date: Jul. 5, 2018

(65) Prior Publication Data
US 2019/0343181 A1 Nov. 14, 2019

(30) Foreign Application Priority Data
Dec. 30, 2016 (EP) .................... 16207600

(51) Int. Cl.
*A24F 40/46* (2020.01)
*A61M 15/06* (2006.01)
(Continued)

(52) U.S. Cl.
CPC ............ *A24F 40/46* (2020.01); *A24F 40/485* (2020.01); *A61M 15/06* (2013.01); *A24D 1/20* (2020.01); *A24F 40/20* (2020.01); *B05B 17/00* (2013.01)

(58) Field of Classification Search
None
See application file for complete search history.

(56) References Cited

U.S. PATENT DOCUMENTS

2003/0154991 A1  8/2003  Fournier et al.
2006/0191546 A1*  8/2006  Takano ................... A24F 42/60
                                                            131/270
(Continued)

FOREIGN PATENT DOCUMENTS

CN          103783674 A       5/2014
EP            3075266 A1     10/2016
(Continued)

OTHER PUBLICATIONS

International Search Report including Written Opinion for PCT/EP2017/084842 dated Apr. 23, 2018.
(Continued)

*Primary Examiner* — Francisco W Tschen
*Assistant Examiner* — Guy F Mongelli
(74) *Attorney, Agent, or Firm* — Lerner David LLP

(57) ABSTRACT

An aerosol generating apparatus, especially a personal vaporizer device such as an electronic smoking article, generates an aerosol from a source of aerosol-forming substance. The aerosol generating apparatus includes a receiving portion configured to receive a consumable unit, such as a charge or cartridge including a source of aerosol-forming substance, and at least one locating member for locating the consumable unit within the receiving portion. The at least one locating member is configured to locate or position the consumable unit within the receiving portion such that an airflow path extends along outer sides of the consumable unit and through the consumable unit entering at one end region thereof and exiting from an opposite end region thereof, with the outer sides of the consumable unit (Continued)

being arranged between the one end region and the opposite end region.

20 Claims, 3 Drawing Sheets

(51) Int. Cl.
    *A24F 40/485*     (2020.01)
    *B05B 17/00*     (2006.01)
    *A24D 1/20*     (2020.01)
    *A24F 40/20*     (2020.01)

(56) References Cited

U.S. PATENT DOCUMENTS

| | | |
|---|---|---|
| 2007/0102013 A1 | 5/2007 | Adams et al. |
| 2014/0270729 A1* | 9/2014 | DePiano ............... A24F 40/40 392/397 |
| 2014/0338686 A1* | 11/2014 | Plojoux ............... A24F 40/485 131/329 |
| 2014/0373856 A1 | 12/2014 | Zuber et al. |
| 2015/0013696 A1 | 1/2015 | Plojoux et al. |
| 2015/0208730 A1 | 7/2015 | Li et al. |
| 2015/0272225 A1 | 10/2015 | Worm et al. |
| 2018/0035709 A1* | 2/2018 | Lara, Jr. ............... A24F 1/16 |
| 2018/0363432 A1* | 12/2018 | Purcell ............... E21B 43/126 |

FOREIGN PATENT DOCUMENTS

| | | | |
|---|---|---|---|
| JP | 2005517421 A | 6/2005 | |
| JP | 2014533513 A | 12/2014 | |
| JP | 2015503336 A | 2/2015 | |
| JP | 2015504667 A | 2/2015 | |
| WO | 2007012007 A2 | 1/2007 | |
| WO | 2015177254 A1 | 11/2015 | |
| WO | WO-2016026810 A1 * | 2/2016 | ........... A24F 47/008 |
| WO | 2016096780 A1 | 6/2016 | |

OTHER PUBLICATIONS

Extended European Search Report including Written Opinion for Application No. EP16207600.4, dated Dec. 6, 2017, pp. 1-14.

* cited by examiner

AEROSOL GENERATING APPARATUSES WITH LOCATING MEMBER AND SUBSTANTIALLY SURROUNDING AIRFLOW PATH OF CONSUMABLE UNIT

CROSS-REFERENCE TO RELATED APPLICATIONS

The present application is a national phase entry under 35 U.S.C. § 371 of International Application No. PCT/EP2017/084842, filed Dec. 29, 2017, published in English, which claims priority to European Patent Application No. 16207600.4 filed Dec. 30, 2016, the disclosures of which are incorporated herein by reference.

BACKGROUND OF THE INVENTION

The present invention relates to an aerosol generating apparatus, and especially to a personal vaporizer device, such as an electronic smoking article, as well as to a consumable unit for use in such an aerosol generating apparatus.

Personal vaporizer devices, such as electronic cigarettes or "e-cigarettes" as they are also known, have gained in popularity over the past ten years as an alternative to traditional smoking articles, like cigarettes, cigars, and cigarillos.

BRIEF SUMMARY OF THE INVENTION

In view of the above, an object of the invention is to provide a new and improved aerosol generating apparatus, especially a new and improved personal vaporizer device, such as an electronic smoking article. In particular, it would be desirable to provide such a personal vaporizer device which is more energy efficient, provides a more optimal vapour and flavour generation and which allows greater control of the aerosol generation. It would also be useful to provide a new and improved consumable unit for such an aerosol generating apparatus or personal vaporizer device, such as a cartridge, capsule or charge of a flavour source, and especially a solid flavour source.

In accordance with the present invention, an aerosol generating apparatus, such as a personal vaporizer device, and especially an electronic smoking article, as recited, for example, in claim 1 is provided. Also, in accordance with the invention, an aerosol generating system as recited, for example, in claim 10, as well as a method of generating an aerosol as recited, for example, in claim 15 is provided. Various preferred and/or advantageous features of the invention are recited in the dependent claims.

According to one aspect, therefore, the present invention provides an aerosol generating apparatus, especially a personal vaporizer device such as an electronic smoking article, for generating an aerosol from a source of an aerosol-forming substance. The apparatus comprises a receiving portion defining a space or cavity configured to receive a consumable unit comprising a body or charge of aerosol-forming substance, and at least one locating member for locating the consumable unit within the receiving portion. In this regard, the receiving portion is typically formed or provided within a housing or casing of the aerosol generating apparatus. The at least one locating member is configured to extend into the consumable unit when the consumable unit is received within the space or cavity of the receiving portion. Furthermore, the at least one locating member is preferably configured to transmit heat to the consumable unit.

According to another aspect, the present invention provides an aerosol generating apparatus, especially a personal vaporizer device such as an electronic smoking article, for generating an aerosol from a source of an aerosol-forming substance. The aerosol generating apparatus comprises a receiving portion configured to receive a consumable unit, such as a charge or cartridge comprising a solid source of aerosol-forming substance. The aerosol generating apparatus further comprises at least one locating member for locating the consumable unit within the receiving portion. The at least one locating member is configured to locate or position the consumable unit within the receiving portion such that an airflow path extends along outer sides of the consumable unit and through the consumable unit entering at one end region thereof and exiting from an opposite end region thereof.

The outer sides of the consumable unit are arranged between the one end region and the opposite end region. The airflow along the airflow path is therefore in direct contact with the outer sides of the consumable unit such that thermal energy can be transferred from heated side walls of the receiving portion via the airflow to the outer sides of the consumable unit and, hence, into the consumable. Due to the airflow substantially surrounding the outer sides of the consumable unit along substantially the whole extension of the consumable unit between the one end region and the opposite end region, a more uniform heating of the consumable may be achieved.

The invention does not only permit precise positioning of the consumable unit within the aerosol generating apparatuses according to any of the aforementioned aspects of the invention, but can also ensure a more uniform and/or more efficient heating of the aerosol-forming substance. It will be noted that the consumable unit may preferably take the form of a disposable or replaceable cartridge, capsule or pod for use in the aerosol generating apparatus according to any of the aforementioned aspects of the invention.

In a preferred embodiment, the at least one locating member may comprise, or be formed as, a projection or an elongate member which is configured and arranged to extend into the body or charge of aerosol-forming substance in the consumable unit. The projection or elongate member preferably includes a tip configured for penetrating into the body or charge of aerosol-forming substance. For example, the at least one locating member may comprise a projection or elongate member which extends from a base of the space or cavity in the receiving portion and is configured to extend into an end region of the consumable unit. Alternatively, or in addition, at least one locating member for locating the consumable unit within the receiving portion may be provided externally of the consumable unit for contact with outer sides of the consumable unit received within the space or cavity of the receiving portion. In one particular embodiment, the at least one locating member may extend into both the one end region and the opposite end region of the consumable unit when the consumable unit is received within a space or cavity of the receiving portion.

In a particularly preferred embodiment, the at least one locating member may be directly heated by conductive coupling to a heating element, such as to walls of the receiving portion defining the space or cavity within which the consumable unit is received. It may also be indirectly heated by the heated airflow (e.g. which may have previously been heated by the walls of the receiving portion). A good thermal conductor is therefore a suitable material for the locating member. Furthermore, the at least one locating member may be hollow or define a channel there-through for conveying or transmitting air into and/or through the body or charge of aerosol-forming substance in the consumable unit. In this regard, the locating member may comprise a pipe or conduit and be suitably sized to fit a recess, e.g. in a base of the consumable unit. The at least one locating member may include apertures, e.g. in the periphery of a pyramid or code shape through which airflow may exit the locating member and flow into the consumable unit.

In a preferred embodiment, the receiving portion forms or provides an airflow path that substantially surrounds the consumable unit when the consumable unit is received within the space or cavity. In particular, the receiving portion may form or define an airflow path which extends along outer sides of the consumable unit received within the space or cavity and which passes through the consumable unit such that the airflow enters at one end region of the consumable unit and exits from an opposite end region thereof. To this end, the at least one locating member may be configured to direct airflow along the airflow path to enter the consumable unit at the one end region thereof. By providing an airflow inlet and an airflow outlet at opposite end regions of the consumable unit, a more uniform heating of the aerosol-forming substance and a more consistent aerosol generation and flavour extraction can be achieved.

In a preferred embodiment, the space or cavity in the receiving portion is defined by side walls which substantially surround the consumable unit when it is received within the space or cavity. The at least one locating member is arranged to locate or position the consumable unit within the space or cavity such that an airflow path travels or extends along the side walls surrounding the consumable unit. The side walls of the receiving portion are preferably configured to transmit heat (e.g. by conduction and/or by radiation) to the airflow and/or to the consumable unit. In this regard, the apparatus is configured to heat the consumable unit to generate the aerosol from the aerosol-forming substance. The heating arrangement or heating device in the apparatus may, for example, be configured similar to that described in the international patent publication WO 2007/012007 A2, the entire contents of which are incorporated herein by reference.

In a preferred embodiment, the receiving portion comprises cap or cover which extends over and/or covers the consumable unit at an upper part of the receiving portion. The cap or cover may include attachment means for engagement with and attachment to an end region of the consumable unit (e.g. the opposite end region). The attachment means may be configured for a press fit, a screw fit, or a bayonet fit with the end region of the consumable unit and/or with the upper part of the receiving portion. Thus, the attachment means may operate or function as the at least one locating member. The consumable unit is desirably positioned or located in the receiving portion such that the one end region of the consumable unit is essentially unobstructed so that airflow can pass uniformly into the inlet end of the consumable unit.

According to another aspect, the present invention provides an aerosol generating apparatus, especially a personal vaporizer device such as an electronic smoking article, comprising a receiving portion configured to receive a consumable unit, such as a charge or body comprising a solid source of aerosol-forming substance, and at least one locating member for locating or positioning the consumable unit within the receiving portion. The at least one locating member is configured to locate or position the consumable unit within the receiving portion such that an air-flow path extends firstly along outer sides of the consumable unit and then through the consumable unit, with the airflow entering at one end region of the consumable unit and exiting from an opposite end region thereof. This enables the charge or body of aerosol-forming substance in the consumable unit to be in contact with the airflow both externally and internally, which thus provides for an increased surface contact with the airflow, and a more efficient and an enhanced aerosol generation.

In a particularly preferred embodiment, the airflow path extending along the outer sides of the consumable unit substantially surrounds the consumable unit when the consumable unit is received within the receiving portion. The surface contact with the airflow can thereby be maximized. As noted above, the consumable unit is configured to be heated in order to generate the aerosol from the aerosol-forming substance. In this regard, the airflow may be heated by the heating arrangement or the heating device in the apparatus before and/or as the airflow passes around and through the consumable unit received within the receiving portion.

In a preferred embodiment, the aerosol generating apparatus includes an airflow by-pass arrangement configured to introduce fresh air into the aerosol stream at a position downstream of the consumable unit. To this end, the airflow path includes a conduit system with one or more valves in the airflow path which regulates a by-pass flow of the air into the airflow path downstream of the receiving portion. This conduit system enables control of aerosol concentration and the flow resistance. The valve(s) may also regulate the flow of heated air to the consumable unit.

According to a further aspect, the present invention provides a consumable unit for an aerosol generating apparatus, and especially a personal vaporizer device. The consumable unit comprises a body or charge of an aerosol-forming substance for receipt in the apparatus, wherein the body or charge is permeable to a flow of air and has an airflow inlet at one end region and an airflow outlet at an opposite end region thereof. In this regard, the consumable unit preferably takes the form of a disposable and/or replaceable cartridge, capsule, or pod of the aerosol-forming substance which typically includes a flavour source for a user.

In a preferred embodiment, the airflow inlet comprises a recess or an indentation formed in the one end region of the body or charge. The recess or indentation has the effect of increasing a surface area of the body or charge of aerosol-forming substance exposed to the airflow, and thus also to heating. As noted above, this recess or indentation may be configured to receive at least one locating member, which may, in turn, also form a heating member for transmitting heat to an internal area of the body or charge of aerosol-forming substance.

In a preferred embodiment, the recess or indentation formed in the one end region of the body or charge is configured to substantially correspond in shape to the at least one locating member received therein. To this end, the recess or indentation formed in the one end region of the body or charge of aerosol-forming substance may, for example, be at least partially conical or at least partially spherical. The recess or indentation may include at least one surface configured to abut against the locating member of the apparatus. For example, the recess or indentation may include a generally flat or planar face for abutting against a locating member of the apparatus. The body or charge of the aerosol-forming substance may include an internal structure, e.g. a mesh, for maintaining a shape of the recess or indentation in the consumable unit. Alternatively, the shape of the recess or indentation may be maintained by material properties of the body or charge of the aerosol-forming substance, e.g. it may be moulded or pressed into this shape. The indentation allows a greater surface area of the aerosol-forming substance to be exposed to heat (i.e. heat from the locating member and/or from the air). More uniform heating enables better extraction and a more consistent aerosol formation. In a further variation, the recess or indentation in the one end region of the consumable unit may continue through the body or charge of the aerosol-forming substance to the opposite end region in the manner of an airflow channel or passage. In this way, the channel or passage formed by this recess may further enhance the air contact surface area and thus the uniformity of heat transfer.

In a preferred embodiment, the body or charge of the aerosol-forming substance comprises tobacco or a tobacco-based material, glycerine, and propylene glycol, and optionally one or more flavourings, which can be vaporized to form an aerosol. The body or charge of the aerosol-forming substance may be formed as a foam or as porous substrate.

In a preferred embodiment, the consumable unit comprises a case or a wrapper which surrounds and/or substantially encloses the body or charge of the aerosol-forming substance. The case or wrapper may thus package the body or charge of the aerosol-forming substance, which in turn may help to ensure its freshness and its freedom from contamination, while also making the handling of the consumable unit easier for a user. In particular, the case or wrapper may hermetically seal the body or charge of aerosol-forming substance to retain product freshness. The seal may be perforated or broken by the at least one locating member (or by another member) upon contact therewith. Other perforations may also be provided to form the airflow and aerosol outlet. Alternatively, or in addition, each consumable unit may also be individually or wrapped in a film or foil packaging wrapper to provide a hermetically sealed enclosure; for example, in a manner similar to a dishwasher tablet.

In some embodiments of the aerosol generating apparatus the at least one locating member may be configured to extend into the one end region and/or the opposite end region of the consumable unit when the consumable unit is received within a space or cavity of the receiving portion.

In some embodiments of the aerosol generating apparatus the at least one locating member may be configured to transmit heat to the consumable unit.

In some embodiments of the aerosol generating apparatus the airflow path may substantially surround the consumable unit when the consumable unit is received within the receiving portion.

In some embodiments of the aerosol generating apparatus the locating member may be configured to direct airflow along the airflow path to enter the consumable unit at the one end region of the consumable unit.

In some embodiments of the aerosol generating apparatus a space or cavity in the receiving portion may be defined by side walls of the receiving portion. In some preferred embodiments, the locating member may be arranged to locate or position the consumable unit within the space or cavity such that the airflow path travels or extends along the side walls. In some embodiments the side walls may be configured to transmit heat to the airflow.

In some embodiments of the aerosol generating apparatus the side walls may substantially surround the consumable unit when the consumable unit is received within the space or cavity.

In some embodiments of the aerosol generating apparatus, the aerosol generating apparatus may further comprise a housing enclosing the receiving portion, the housing including at least one housing inlet in fluid communication with the airflow path and being spaced from the side walls of the receiving portion.

In some embodiments of the aerosol generating apparatus the at least one housing inlet may be positioned at the same axial height of the housing as an air inlet into the receiving portion or at a different axial height of the housing as an air inlet into the receiving portion.

According to yet another aspect, the invention also provides an aerosol generation system for generating an aerosol from an aerosol-forming substance. The system comprises an aerosol generating apparatus according to any of the embodiments described above, and a consumable unit comprising a body or charge of aerosol-forming substance, especially according to any one of the embodiments described above.

In some embodiments of the aerosol generating system the consumable comprises a body or charge of a solid aerosol-forming substance for receipt in the apparatus, the body or charge being permeable to a flow of air and having an airflow inlet at one end region and an airflow outlet at an opposite end region thereof.

In some embodiments of the aerosol generating system the consumable unit may comprise an airflow inlet with a recess or indentation formed in the one end region of the body or charge.

In some embodiments of the aerosol generating system the recess or indentation formed in the one end region of the body or charge may be configured to receive the locating member of the apparatus. In some preferred embodiments of the aerosol generating system, the recess or indentation may substantially correspond in shape to the locating member.

According to still a further aspect, the invention provides a method of generating an aerosol, especially in a vaporizer device such as an electronic smoking article, the method comprising the steps of:

providing a consumable unit having a body or charge of an aerosol-forming substance, especially a solid aerosol-forming substance;

introducing the consumable unit into a receiving portion of an aerosol generating apparatus;

heating the consumable unit in the receiving portion of the aerosol generating apparatus; and directing air along an airflow path over outer sides of the consumable unit and through the consumable unit, with the airflow path entering at one end region of the body or charge and exiting from an opposite end region thereof. The outer sides may be arranged between the one end region and the opposite end region.

In a preferred embodiment, the method further comprises the step of: inserting or arranging at least one locating member in an end region of the consumable unit to position or locate the consumable unit within the receiving portion. The end region of the consumable unit preferably includes a recess or indentation for receiving the locating member, whereby the recess or indentation preferably has a shape which substantially corresponds to a shape of the at least one locating member.

In a preferred embodiment, the method further comprises the step of: transmitting or applying heat to the consumable unit via a locating member to generate an aerosol from the body or charge of aerosol-forming substance at least one locating member in an end region of the consumable unit to position or locate the consumable unit within the receiving portion.

According to still a further aspect, the invention provides a method of generating an aerosol, especially in a vaporizer device such as an electronic smoking article, the method comprising the steps of:

provide a consumable unit having a body or charge of an aerosol-forming substance, especially a solid aerosol-forming substance;

introducing the consumable unit into a receiving portion of an aerosol generating apparatus;

inserting or arranging at least one locating member in an end region of the consumable unit to position or locate the consumable unit within the receiving portion; and heating the consumable unit in the receiving portion of the apparatus, the heating including applying heat to the consumable unit via the at least one locating member to generate an aerosol from the body or charge of the aerosol-forming substance.

In a preferred embodiment, the end region of the consumable unit includes a recess or indentation for receiving the at least one locating member. The recess or indentation preferably corresponds in shape to the locating member. In this way, the surface area of the body or charge of aerosol-forming substance which is heated by the locating member can be maximised.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which.

DETAILED DESCRIPTION

Figure 1:
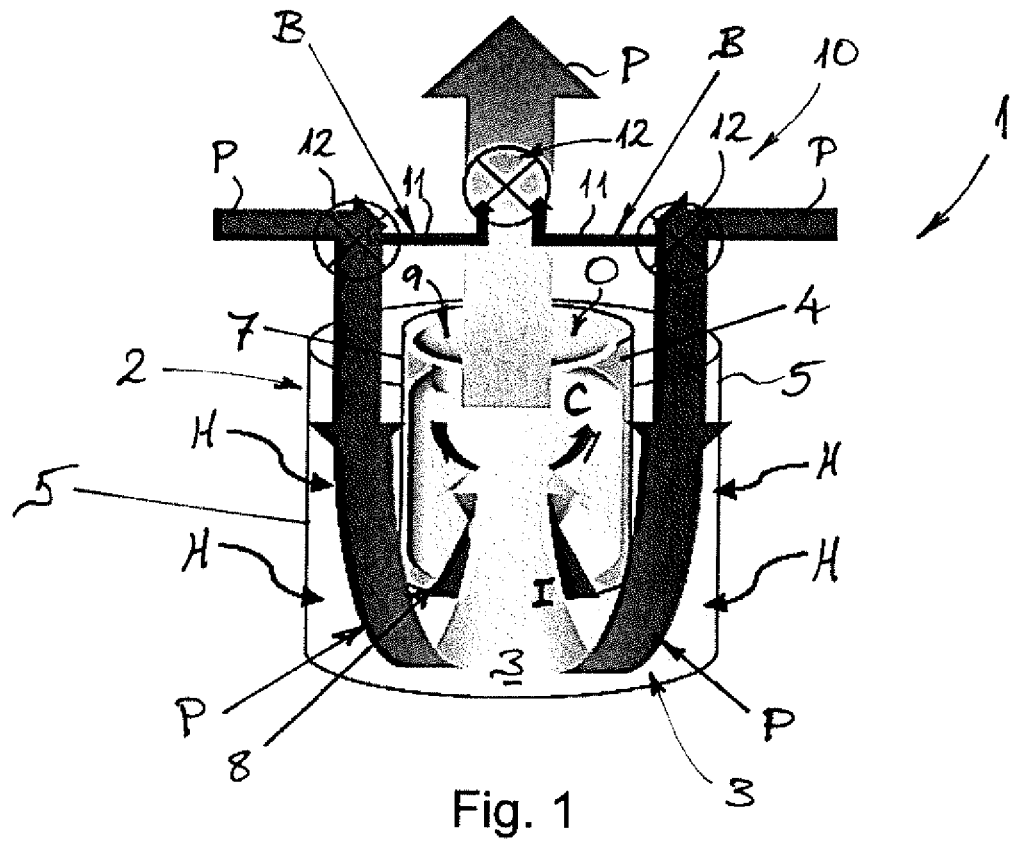
FIG. 1 is a schematic side view of part of an aerosol generating apparatus, such as an electronic smoking article, according to an embodiment, and a consumable unit according to an embodiment received therein.

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will further be appreciated that certain actions and/or steps in an embodiment of a method may be described or depicted in a particular order of occurrences while those skilled in the art will understand that such specificity with respect to sequence is not actually required. It will also be understood that the terms and expressions used in the present specification have the ordinary meaning as is accorded to such terms and expressions with respect to their corresponding respective areas of inquiry and study, except where specific meanings have otherwise been set forth herein.

As used herein "aerosol forming substance" may include a carrier material, which may include a mixture of propylene glycol (PG) and/or glycerin (G). Preferably, the carrier material has a composition of at least 20 wt %. The aerosol forming substance may in addition include ground tobacco particles (e.g. in addition to the carrier material). The aerosol forming material may include other materials, such as a flavourant, water etc.

As used herein, the term "aerosol generation apparatus" or "apparatus" may include smoking apparatus to deliver an aerosol to a user, including an aerosol for smoking, by means of an aerosol generating unit (e.g. a heater or atomiser which generates a vapour which condenses into an aerosol before delivery to an outlet of the apparatus at, for example, a mouthpiece, for inhalation by a user). An aerosol for smoking may refer to an aerosol with particle sizes of 0.5-7 microns. The particle size may be less than 10 or 7 microns. The apparatus may be portable. Portable may refer to the apparatus being for use when held by a user. The apparatus may be adapted to generate a variable amount of aerosol, e.g. by activating an atomizer for a variable amount of time (as opposed to a metered dose of aerosol), which can be controlled by a trigger. The trigger may be user activated, such as by a vaping button and/or inhalation sensor. The inhalation sensor may be sensitive to the strength of inhalation as well as the duration of inhalation so as to enable more or less vapour to be provided based on the strength of inhalation (so as to mimic the effect of smoking a conventional combustible smoking article such as a cigarette, cigar or pipe, etc.). The apparatus may include a temperature regulation control such as for example a Proportional, Integral, Differential (PID) controller to quickly drive the temperature of the heater and/or the heated aerosol generating substance (aerosol pre-cursor) to a specified target temperature and thereafter to maintain the temperature at the target temperature regardless of the amount of aerosol pre-cursor available at the aerosol generating apparatus and regardless of the strength with which a user inhales.

With reference to FIG. 1 of the drawings, part of an aerosol generating apparatus 1 in the form of a personal vaporizer device is illustrated. The apparatus or vaporizer device 1 comprises a receiving portion 2 which defines a space or cavity 3 and is configured to receive a consumable unit 4 provided in the form of a disposable and/or replaceable cartridge, capsule, or pod containing an air-permeable body or charge C of an aerosol-forming substance S. The receiving portion 2 is typically formed or provided within a housing or casing (reference sign 17 in FIGS. 6 and 7, but not explicitly shown in FIGS. 1, 2 and 3) of the apparatus or vaporizer device 1. In this embodiment, the space or cavity 3 of the receiving portion 2 is generally cylindrical in shape and is defined by side walls 5. The capsule or pod 4 is also generally cylindrical.

Within the generally cylindrical space or cavity 3 of the receiving portion 2, one or more locating member(s) 6 is/are provided for locating or positioning the capsule or pod 4 within the receiving portion 2. In this regard, the locating member 6 is configured to locate or position the capsule or pod 4 such that an air-flow path P through the apparatus or vaporizer device 1 extends along cylindrical outer sides 7 of the capsule or pod 4 and then through the capsule or pod 4. In this regard, the airflow path P substantially surrounds the cylindrical capsule or pod 4 and flows through the annular space between the pod 4 and the side walls 5 when the pod 4 is received within space or cavity 3 of the receiving portion 2. The airflow then enters the capsule or pod 4 via an inlet I at one end region 8 and exits from the capsule or pod 4 via an outlet O at an opposite end region 9 thereof.

The aerosol generating apparatus or vaporizer device 1 is configured to heat the capsule or pod 4 to generate an aerosol from the aerosol-forming substance. In particular, the capsule or pod 4 is heated to generate an aerosol in the absence of combustion, e.g. at a temperature in the range of about 150° C. to 350° C. As such, the apparatus or vaporizer device 1 includes a heating arrangement which may, for example, be configured similar to that described in international patent publication WO 2007/012007 A2. The side walls 5 of the receiving portion 2 may for example be conductively coupled to a heater element (not shown) which may heat up the side walls 5. The side walls 5 of the receiving portion 2 are configured to transmit heat H from the heating arrangement or heater element (not shown) both by conduction and by radiation to an airflow travelling along the airflow path P and to the capsule or pod 4. In this way, the charge or body of aerosol-forming substance S in the capsule or pod 4 is heated and is in contact with the heated airflow both externally and internally, which in turn provides for a high surface contact with the airflow, and a very efficient aerosol generation.

The aerosol generating apparatus or vaporizer device 1 further includes an airflow by-pass arrangement 10 configured to introduce fresh air into the airflow path P at a position downstream of capsule or pod 4. In this way, by-pass arrangement 10 includes a conduit system 11 with valves 12 in the airflow path P which control or regulate a by-pass flow B of fresh air into the airflow path P downstream of the capsule or pod 4. This, in turn, enables control of aerosol concentration in the air-flow path P and of the flow resistance. The valve(s) 12 may also be used to control or regulate the flow of heated air to the capsule or pod 4.

Figure 2:
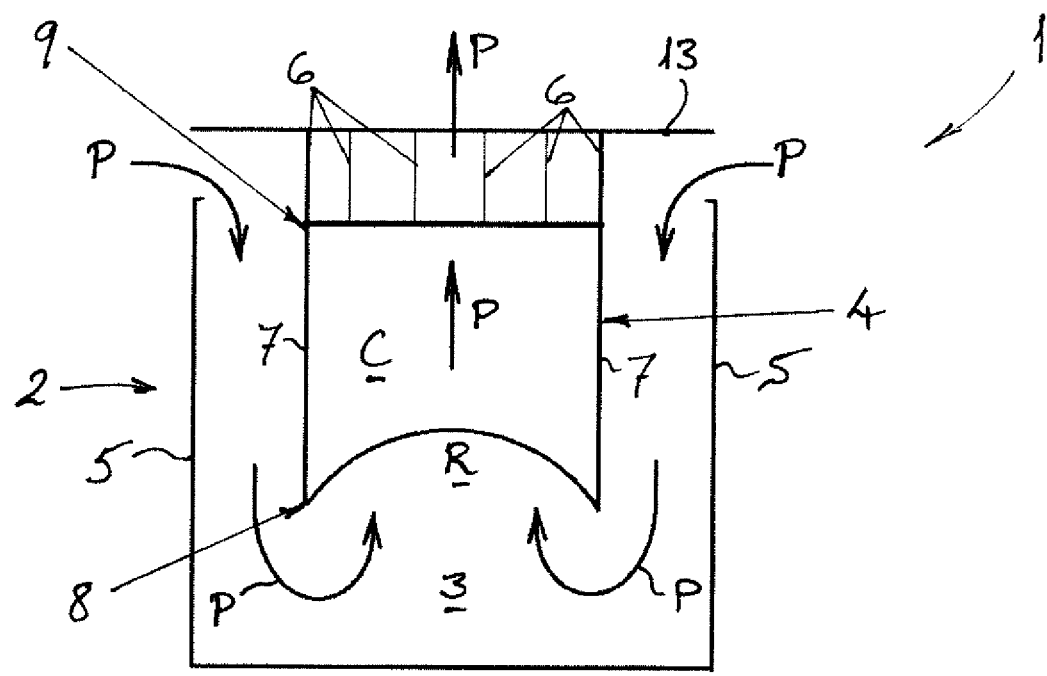
FIG. 2 is a schematic side view of part of an aerosol generating apparatus, such as an electronic smoking article, of another embodiment, with a consumable unit of another embodiment received therein.
Figure 3:
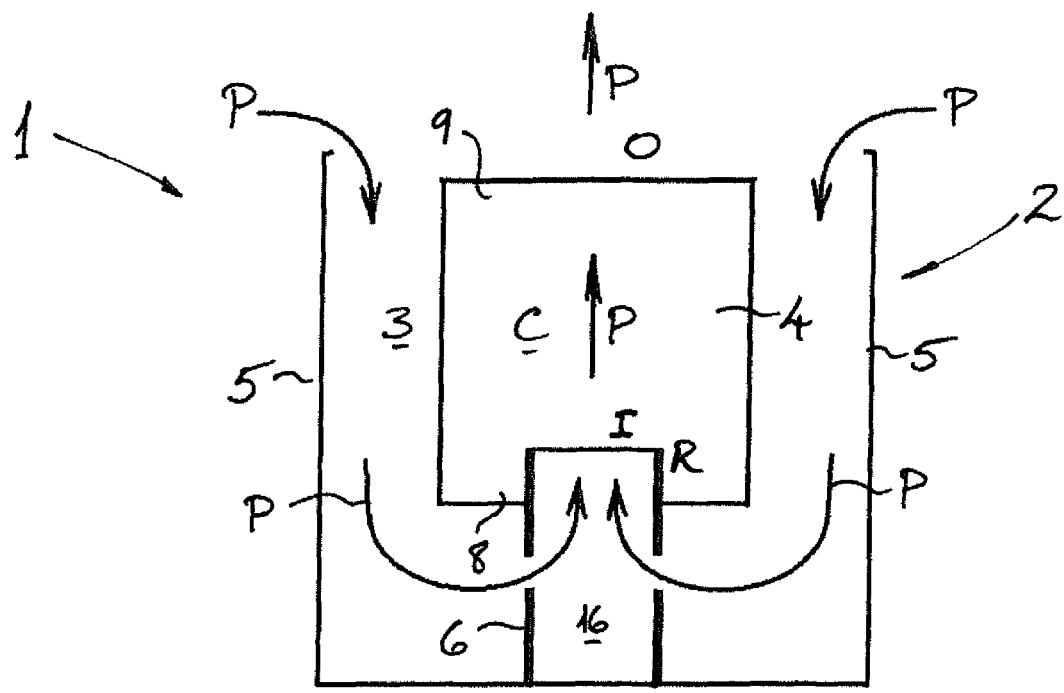
FIG. 3 is a schematic side view of part of an aerosol generating apparatus, such as an electronic smoking article, of a further embodiment, with a consumable unit of a further embodiment received therein.

With reference to FIG. 2 of the drawings, alternative embodiments of an aerosol generating apparatus 1 and a consumable unit 4 according to the invention are illustrated. In this embodiment, the receiving portion 2 includes a cover member 13 to which the consumable unit 4—again provided in the form of a disposable and/or replaceable cartridge, capsule, or pod—is attached. The attachment means may be configured for a press fit, a screw fit, or a bayonet fit with one end region 9 (exemplarily illustrated as upper end region 9 in FIG. 2) of the capsule or pod 4. Thus, the attachment means in this embodiment acts as one more locating member(s) 6 for locating or positioning the capsule or pod 4 in the cylindrical space or cavity 3 of the receiving portion 2 to provide an airflow path P as described previously.

Figure 6:
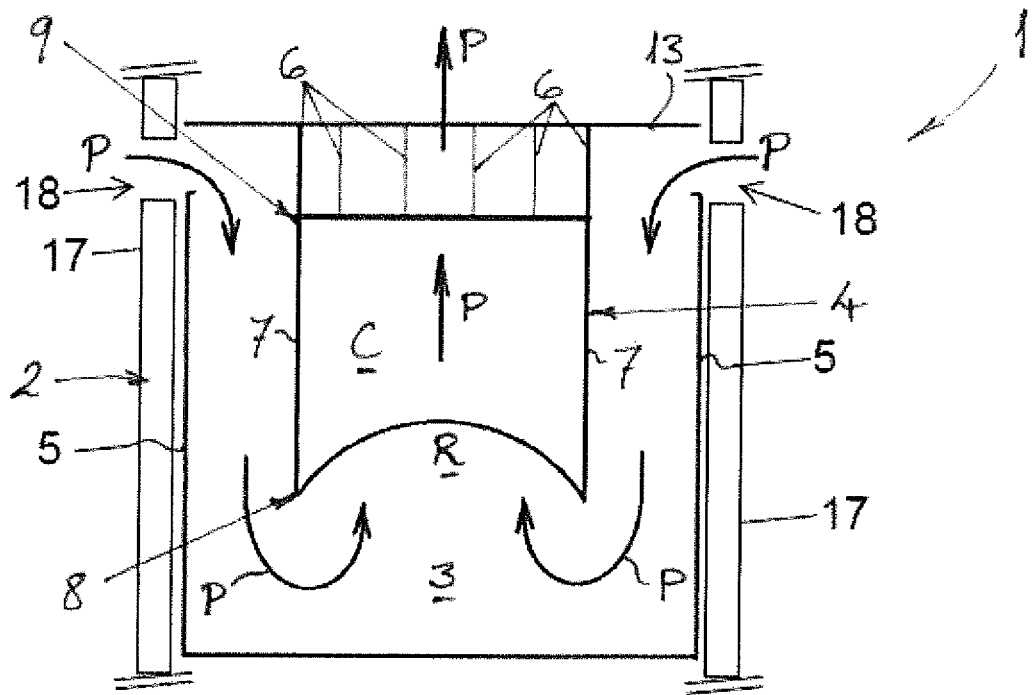
FIG. 6 is a schematic side view of part of an aerosol generating apparatus, such as an electronic smoking article, of another embodiment, with a consumable unit of another embodiment received therein.
Figure 7:
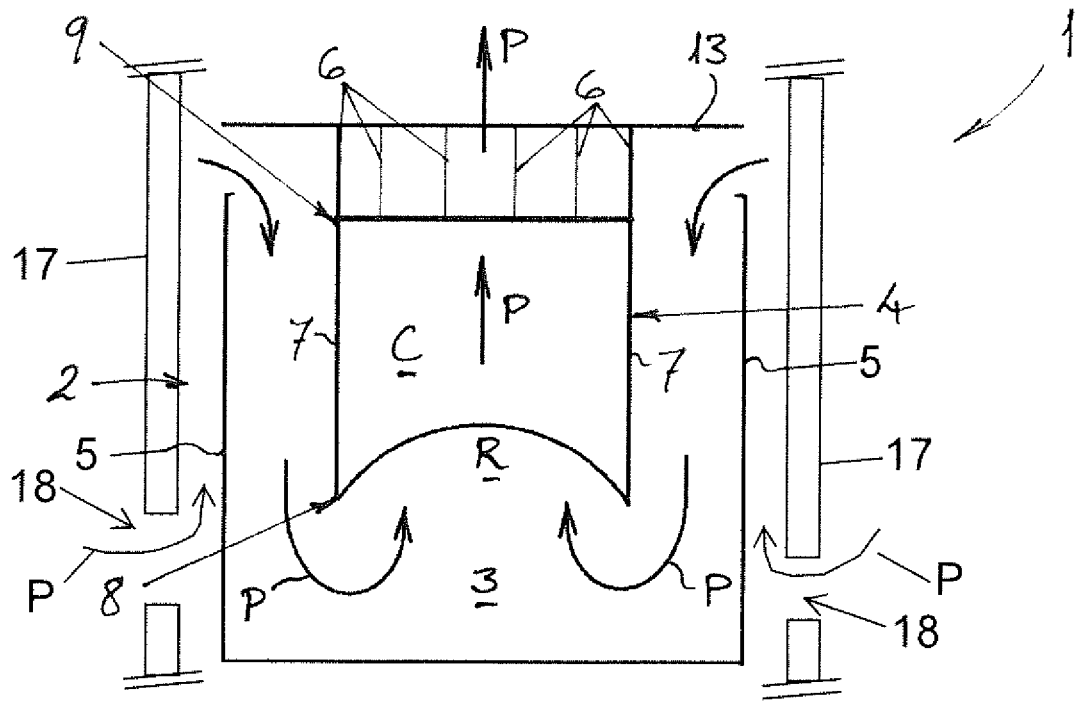
FIG. 7 is a schematic side view of part of an aerosol generating apparatus, such as an electronic smoking article, of another embodiment, with a consumable unit of another embodiment received therein.

As shown in FIGS. 6 and 7, the housing 17 of the aerosol generating apparatus or vaporizer 1 may enclose the receiving portion 2 in such a way that air streaming from the outside of the aerosol generating apparatus or vaporizer 1 into the apparatus 1 enters the housing 17 at at least one housing inlet 18 formed or provided in the housing body, streams through the space between the housing 17 and the side walls 5 of the receiving portion 2 into the receiving portion 2 at respective air inlets thereof and into the space or cavity 3 of the receiving portion 2. The whole stream of air from the outside of the apparatus 1 and through the consumable unit 4 is generally referred to as airflow path P.

As exemplarily depicted in FIG. 6, the at least one housing inlet 18 may be provided at substantially the same axial position as the air inlet of the receiving portion 2, i.e. the interface position between the cover member 13 and the side walls 5 of the receiving portion 2. That way, the air streaming through the at least one housing inlet 18 may substantially directly enter the air inlet of the receiving portion without having to travel along the outer side walls 5 of the receiving portion 2.

As exemplarily depicted in FIG. 7, an alternative positioning of the at least one housing inlet 18 may substantially offset the at least one housing inlet 18 along the length axis of the apparatus 1 with respect to the axial position of the air inlet of the receiving portion 2, i.e. the interface position between the cover member 13 and the side walls 5 of the receiving portion 2. That way, the air streaming through the at least one housing inlet 18 needs to at first stream a certain distance along the outer side walls 5 of the receiving portion 2 before being able to enter the air inlet of the receiving portion 2.

The housing inlets 18 may for example be formed as holes or openings in the housing body 17 and may for example be equally distributed around the radial circumference of the housing 17. In case of a cylindrical housing 17 the housing inlets 18 may be formed as a ring of holes or openings around the housing body at substantially the same axial height. The number of housing inlets 18 may be limited to one, but may also be two or more. In the exemplary embodiments of FIGS. 6 and 7, there are two housing inlets 18 shown, one on each side of the apparatus 1. However, more than two housing inlets 18 may be provided in the housing body 17, for example an even number such as four, six, eight, ten or twelve. The housing inlets 18 may have any shape as desired or appropriate in order to ensure an unperturbed airflow therethrough. The housing inlets 18 may for example be circular, elliptical or rectangular in cross-section and may for example be implemented as slits, vias or similar openings in the housing body 17.

Figure 4:
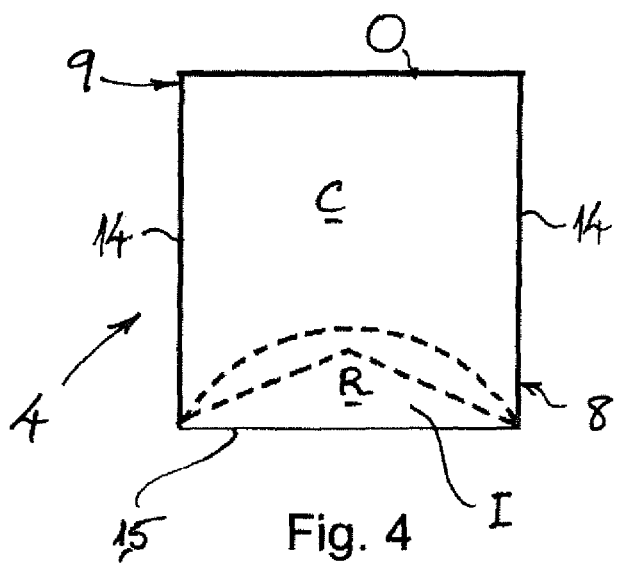
FIG. 4 is a schematic side view of a consumable unit, especially a cartridge, for a personal vaporizer device according to an embodiment.
Figure 5:
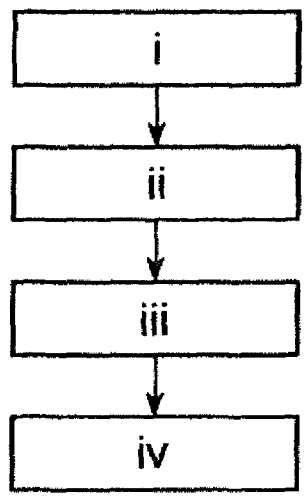
FIG. 5 is a flow diagram which schematically represents a method according to an embodiment of the invention.

In this embodiment of FIG. 2 and optionally FIGS. 6 and 7, the capsule or pod 4 includes a recess or indentation R formed in its one end region 8 to form the airflow inlet I. With reference also to FIG. 4 of the drawings, it will be noted that the recess or indentation R may, for example, be partially conical or partially spherical and has the effect of increasing a surface area of the body or charge C of aerosol-forming substance exposed to the airflow, and thus also to heating. This recess or indentation R formed in the one end region 8 of the capsule or pod 4 may be shaped to essentially correspond to a locating member 6 which may be received therein. As is also apparent from FIG. 4, the capsule or pod 4 may include a case or wrapper 14 which surrounds and/or substantially encloses the body or charge C of aerosol-forming substance. The case or wrapper 14 may thus package the body or charge C of the aerosol-forming substance S and help to ensure that is remains both fresh and free from contamination, while also making the handling of the capsule or pod 4 easier for a user. A removable film or foil cover 15 may also be provided covering the recess or indentation R for removal by a user prior to introducing the capsule or pod 4 into the apparatus or vaporizer device 1.

Referring to FIGS. 3 and 4, embodiments of an aerosol generating apparatus 1 and of a consumable unit 4 according to the invention are illustrated. In this particular case, a locating member 6 is configured to extend into the capsule or pod 4 when the capsule or pod 4 is received within the space or cavity 3 of the receiving portion 2. That is, the locating member 6 is formed as a projection from a base of the space or cavity 3 and is configured and arranged to extend into a recess R formed in the end region 8 of the capsule or pod 4. As can be seen, the locating member 6 is hollow and defines a channel 16 there-through for airflow into and/or through the body or charge of aerosol-forming substance S in the capsule or pod. The side walls 5 of the receiving portion 2 may again be conductively coupled to a heater element (not shown) which may heat up the side walls 5. In addition to heating via the side walls 5 of the receiving portion 2, the locating member 6 in this embodiment is configured to transmit heat to the capsule or pod 4 and is formed of a material which is a good thermal conductor. To this end, the locating member 6 may be connected to an electrically resistive heating element (not shown) which transmits heat to the locating member 6 via conduction. It will be noted that, instead of a pipe shape, the locating member 6 could alternatively be formed as a spike with a sharp tip configured for penetrating into the body or charge of aerosol-forming substance S. The recess or indentation R in the one end region 8 of the capsule or pod 4 may optionally continue through the body or charge C of the aerosol-forming substance to the opposite end region 9 to provide an airflow channel or passage from an inlet I to an outlet of the consumable unit 4 there-through. In this way, the channel or passage formed by the recess R may increase the contact surface area with the airflow and thus the heat transfer. Such a channel or passage could be press-formed in the body or charge C of the aerosol-forming substance. It may as well be possible for the locating member 6 or at least a portion of the locating member 6 to extend from the end region 8 through the whole capsule or pod 4 to the opposite end region 9.

Referring to FIG. 5 of the drawings, a flow diagram is shown that illustrates schematically steps in a method of generating an aerosol in a personal vaporizer device 1, especially in an electronic smoking article according to the embodiments of the invention described above with respect to FIGS. 1 to 4. In this regard, the first box i of FIG. 5 represents the step of providing a consumable unit 4, such as a capsule or pod, having an air-permeable body or charge C of an aerosol-forming substance, especially a solid aerosol-forming substance, such as a tobacco foam. The second box ii represents the step of introducing the consumable unit 4 into a receiving portion 2 of an aerosol generating apparatus or vaporizer device 1. The third box iii represents the step of heating the consumable unit 4 in the receiving portion 2 of the aerosol generating apparatus 1. The final box iv in FIG. 5 of the drawings represents the step of directing air along an airflow path P over outer sides 7 of the consumable unit 4 and through the consumable unit 4, with the airflow path P entering at one end region 8 of the body or charge C and exiting from an opposite end region 9 thereof. The outer sides 7 are arranged between the one end region 8 and the opposite end region 9.

According to an alternative aspect, however, the method of generating an aerosol schematically illustrated in FIG. 5 of the drawings may include different steps in the third and fourth boxes iii and iv. In particular, the third box iii may represent the step of inserting or arranging at least one locating member 6 in the said one end region 8 of the consumable unit 4 to position or locate the consumable unit within the receiving portion 2. Further, the fourth box iv in FIG. 5 of the drawings may represent the step of heating the consumable unit 4 in the receiving portion 2 of the apparatus 1, whereby the heating includes applying heat to the consumable unit 4 via the at least one locating member 6 to generate an aerosol from the body or charge C of the aerosol-forming substance.

Although specific embodiments of the invention are illustrated and described herein, it will be appreciated by those of ordinary skill in the art that a variety of alternate and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

Further embodiments of the present invention are given in the following:

Embodiment 1

An aerosol generating apparatus for generating an aerosol from an aerosol-forming substance, the apparatus comprising:

a receiving portion defining a space or cavity configured to receive a consumable unit comprising a body or charge of aerosol-forming substance, and at least one locating member for locating the consumable unit within the receiving portion, wherein the at least one locating member is configured to extend into the consumable unit when the consumable unit is received within the space or cavity of the receiving portion, and wherein the at least one locating member is configured to transmit heat to the consumable unit.

Embodiment 2

An aerosol generating apparatus according to embodiment 1, wherein the receiving portion defines an airflow path that substantially surrounds the consumable unit when the consumable unit is received within the space or cavity.

Embodiment 3

An aerosol generating apparatus according to embodiment 1 or 2, wherein the receiving portion defines an airflow path which extends along outer sides of the consumable unit received within the space or cavity of the receiving portion and which passes through the consumable unit with airflow entering at one end region thereof and exiting from an opposite end region thereof.

Embodiment 4

An aerosol generating apparatus according to embodiment 3, wherein the locating member is configured to direct airflow along the air flow path to enter the consumable unit at the one end region thereof.

Embodiment 5

An aerosol generating apparatus according to any one of embodiments 1 to 4, wherein the space or cavity in the receiving portion is defined by side walls which substantially surround the consumable unit when the consumable unit is received within the space or cavity, and wherein the locating member is arranged to locate or position the consumable unit within the space or cavity such that an air flow path travels or extends along the side walls, wherein the side walls are preferably configured to transmit heat to the airflow.

Embodiment 6

An aerosol generating apparatus, comprising:
a receiving portion configured to receive a consumable unit, such as a charge or cartridge comprising a solid source of aerosol-forming substance, and
at least one locating member for locating the consumable unit within the receiving portion,
wherein the at least one locating member is configured to locate or position the consumable unit within the receiving portion such that an air flow path extends along outer sides of the consumable unit and through the consumable unit entering at one end region thereof and exiting from an opposite end region thereof.

Embodiment 7

An aerosol generating apparatus according to embodiment 6, wherein the airflow path that extends along the outer sides of the consumable unit substantially surrounds the consumable unit when the consumable unit is received within the receiving portion.

Embodiment 8

A consumable unit for an aerosol generating apparatus, the consumable unit comprising:
a body or charge of a solid aerosol-forming substance for receipt in the apparatus, the body or charge being permeable to a flow of air and having an airflow inlet at one end region and an airflow outlet at an opposite end region thereof.

Embodiment 9

A consumable unit according to embodiment 8, wherein the airflow inlet comprises a recess or indentation formed in the one end region of the body or charge.

Embodiment 10

A consumable unit according to embodiment 8 or embodiment 9, wherein a recess or indentation formed in the one end region of the body or charge is configured to receive a locating member of the apparatus; wherein the recess or indentation preferably substantially corresponds in shape to the locating member.

Embodiment 11

A consumable unit according to any one of embodiments 8 to 10, wherein a recess or indentation formed in the one end region of the body or charge is at least partially conical or at least partially spherical.

Embodiment 12

A consumable unit according to any one of embodiments 8 to 11, wherein a recess or indentation formed in the one end region of the body or charge has a generally flat or planar base which is configured to abut against a locating member of the apparatus.

Embodiment 13

An aerosol generation system for generation of an aerosol from an aerosol-forming substance, the system comprising:
an aerosol generating apparatus, especially according to any one of embodiments 1 to 7, and
a consumable unit comprising a body or charge of a solid aerosol-forming substance, especially according to any of embodiments 8 to 12.

Embodiment 14

A method of generating an aerosol, especially in a vaporizer device such as an electronic smoking article, comprising the steps of:
introducing a consumable unit into a receiving portion of an aerosol generating apparatus, the consumable unit having a body or charge of an aerosol-forming substance, especially a solid aerosol-forming substance;
heating the consumable unit in the receiving portion of the aerosol generating apparatus; and
directing air along a flow path over outer sides of the consumable unit and through the consumable unit, with the flow path entering at one end region of the body or charge and exiting from an opposite end region thereof.

Embodiment 15

A method according to embodiment 14, further comprising one or more of steps:
inserting or arranging at least one locating member in an end region of the consumable unit to position or locate the consumable unit within the receiving portion, whereby the end region of the consumable unit preferably includes a recess or indentation for receiving the locating member; and/or transmitting or applying heat to the consumable unit via at least one locating member to generate an aerosol from the body or charge of aerosol-forming substance.

Embodiment 16

A method of generating an aerosol, especially in a vaporizer device such as an electronic smoking article, comprising the steps of:

introducing a consumable unit into a receiving portion of an aerosol generating apparatus, the consumable unit having a body or charge of an aerosol-forming substance, especially a solid aerosol-forming substance;

inserting or arranging at least one locating member in an end region of the consumable unit to position or locate the consumable unit within the receiving portion; and heating the consumable unit in the receiving portion of the apparatus, the heating including applying heat to the consumable unit via the at least one locating member to generate an aerosol from the body or charge of the aerosol-forming substance.

LIST OF REFERENCE SIGNS 1 aerosol generating apparatus or personal vaporizer
2 receiving portion
3 space or cavity
4 consumable unit, cartridge, capsule, or pod
5 side walls of receiving portion
6 locating member
7 outer sides of capsule or pod
8 one end region
9 opposite end region
10 by-pass arrangement
11 conduit system
12 valve
13 cap or cover member
14 case or wrapper
15 film or foil cover
16 channel
17 housing
18 housing inlet
C body or charge of aerosol-forming substance
S aerosol-forming substance
P airflow path
H heat
I inlet
O outlet
B by-pass flow
R recess or indentation

The invention claimed is:

1. An aerosol generating apparatus, comprising:
a receiving portion having a space or cavity configured to receive a consumable unit, and
at least one locating member for locating the consumable unit within the space or cavity of the receiving portion,
wherein the at least one locating member is configured to locate or position the consumable unit within the space or cavity of the receiving portion such that when the consumable unit is disposed within the space or cavity of the receiving portion, an airflow path is defined to extend along outer sides of the consumable unit and through the consumable unit entering at one end region thereof and exiting from an opposite end region thereof, the outer sides of the consumable unit being arranged between the one end region and the opposite end region; and
wherein a first portion of the airflow path substantially surrounds the consumable unit when the consumable unit is received within the space or cavity of the receiving portion; and
the receiving portion is elongate in shape along an axis, at least one upstream opening and a downstream opening of the airflow path are defined at a common axial end of the space or cavity of the receiving portion relative to the axis, a segment of the airflow path extends from the at least one upstream opening to the downstream opening, and the segment includes the first portion of the airflow path that substantially surrounds the consumable unit when the consumable unit is received within the receiving portion; and
wherein the at least one locating member is located at the common axial end of the space or cavity of the receiving portion.

2. The aerosol generating apparatus according to claim 1, wherein the at least one locating member is configured to extend into the opposite end region of the consumable unit through an end surface of the opposite end region of the consumable unit when the consumable unit is received within the space or cavity of the receiving portion.

3. The aerosol generating apparatus according to claim 2, wherein the at least one locating member is configured to transmit heat to the consumable unit.

4. The aerosol generating apparatus according to claim 1, wherein the space or cavity in the receiving portion is defined by side walls of the receiving portion, the at least one locating member being arranged to locate or position the consumable unit within the space or cavity such that the airflow path travels or extends along the side walls.

5. The aerosol generating apparatus according to claim 4, wherein the side walls substantially surround the consumable unit when the consumable unit is received within the space or cavity.

6. An aerosol generating system comprising the aerosol generating apparatus according to claim 1 and a consumable unit.

7. The aerosol generating system according to claim 6, wherein the consumable unit includes a body or charge of an aerosol-forming substance for receipt in the apparatus, the body or charge being permeable to a flow of air and having an airflow inlet at one end region of the body and an airflow outlet at an opposite end region of the body.

8. The aerosol generating system according to claim 7, wherein the airflow inlet includes a recess or indentation formed in the one end region of the body or charge.

9. The aerosol generating system according to claim 7, wherein the consumable unit further includes a cartridge containing the body or charge.

10. The aerosol generating apparatus according to claim 1, wherein the at least one locating member is a projection extending from a base of the receiving portion.

11. The aerosol generating apparatus according to claim 10, wherein the projection is hollow and defines a channel therethrough.

12. The aerosol generating apparatus according to claim 11, wherein the projection is pipe shaped.

13. The aerosol generating apparatus according to claim 10, wherein the projection is a spike having a tip configured for penetrating the consumable unit.

14. The aerosol generating apparatus according to claim 1, comprising a cover that is configured to attach to an upper end of the receiving portion that is nearer the opposite end of the consumable unit than the one end of the consumable unit such that the air flow path passes through the cover after exiting the opposite end of the consumable unit.

15. The aerosol generating apparatus according to claim 1, wherein the at least one upstream opening is among a plurality of upstream openings at the common axial end, wherein the plurality of upstream openings is circumferentially distributed around the axis.

16. An aerosol generating apparatus, comprising:
a receiving portion configured to receive a consumable unit, and
at least one locating member for locating the consumable unit within the receiving portion,
wherein the at least one locating member is configured to locate or position the consumable unit within the receiving portion such that when the consumable unit is disposed within the receiving portion, an airflow path is defined to extend along outer sides of the consumable unit and through the consumable unit entering at one end region thereof and exiting from an opposite end region thereof, the outer sides of the consumable unit being arranged between the one end region and the opposite end region; and
wherein a first portion of the airflow path substantially surrounds the consumable unit when the consumable unit is received within the receiving portion; and
the receiving portion is elongate in shape along an axis, at least one upstream opening and a downstream opening of the airflow path are defined in the receiving portion at a common axial end of the receiving portion relative to the axis, a segment of the airflow path extends from the at least one upstream opening to the downstream opening, and the segment includes the first portion of the airflow path that substantially surrounds the consumable unit when the consumable unit is received within the receiving portion;
wherein a space or cavity in the receiving portion is defined by side walls of the receiving portion, the at least one locating member being arranged to locate or position the consumable unit within the space or cavity such that the airflow path travels or extends along the side walls; and
a housing enclosing the receiving portion, the housing including at least one housing inlet in fluid communication with the airflow path and being spaced from the side walls of the receiving portion.

17. The aerosol generating apparatus according to claim 16, wherein the at least one housing inlet is positioned at a different height along the axis of the receiving portion than an air inlet into the receiving portion.

18. The aerosol generating apparatus according to claim 16, wherein the at least one locating member is configured to extend into the one end region of the consumable unit when the consumable unit is received within a space or cavity of the receiving portion.

19. An aerosol generating apparatus, comprising:
a receiving portion configured to receive a consumable unit,
a housing enclosing the receiving portion and including at least one housing inlet where air may enter the housing from outside the aerosol generating apparatus; and
at least one locating member for locating the consumable unit within the receiving portion,
wherein the at least one locating member is configured to locate or position the consumable unit within the receiving portion such that when the consumable unit is disposed within the receiving portion, an airflow path is defined to extend along outer sides of the consumable unit and through the consumable unit entering at one end region thereof and exiting from an opposite end region thereof, the outer sides of the consumable unit being arranged between the one end region and the opposite end region; and
wherein a first portion of the airflow path substantially surrounds the consumable unit when the consumable unit is received within the receiving portion; and
the receiving portion is elongate in shape along an axis, at least one upstream opening and a downstream opening of the airflow path are defined at a common axial end of the receiving portion relative to the axis, a segment of the airflow path extends from the at least one upstream opening to the downstream opening, and the segment includes the portion of the airflow path that substantially surrounds the consumable unit when the consumable unit is received within the receiving portion;
wherein a space or cavity in the receiving portion is defined by side walls of the receiving portion, the at least one locating member being arranged to locate or position the consumable unit within the space or cavity such that the airflow path travels or extends along the side walls;
wherein the at least one housing inlet is positioned at the same height along the axis of the receiving portion as an air inlet into the receiving portion.

20. A method of generating an aerosol, especially in a vaporizer device such as an electronic smoking article, comprising the steps of:
introducing a consumable unit into the space or cavity of the receiving portion of the aerosol generating apparatus of claim 1, the consumable unit having a body or charge of an aerosol-forming substance;
heating the consumable unit in the receiving portion of the aerosol generating apparatus; and
directing air along the airflow path over outer sides of the consumable unit and through the consumable unit, with the airflow path entering at one end region of the body or charge and exiting from an opposite end region thereof, wherein the outer sides are arranged between the one end region and the opposite end region.

* * * * *